United States Patent
Attila

(10) Patent No.: US 7,655,124 B2
(45) Date of Patent: Feb. 2, 2010

(54) APPARATUS TO ASSIST PLATELET MANIPULATION TO PREVENT AND TREAT ENDOVASCULAR DISEASE AND ITS SEQUELAE

(76) Inventor: Mady Attila, 1450 S. Kihei Rd., Suite G104, Kihei, HI (US) 96753

(*) Notice: Subject to any disclaimer, the term of this patent is extended or adjusted under 35 U.S.C. 154(b) by 113 days.

(21) Appl. No.: 11/868,413

(22) Filed: Oct. 5, 2007

(65) Prior Publication Data
US 2009/0090671 A1    Apr. 9, 2009

(51) Int. Cl.
*B03C 5/02* (2006.01)
*C02F 1/48* (2006.01)
(52) U.S. Cl. .............. 204/571; 210/243; 204/572; 204/450; 209/128; 435/372
(58) Field of Classification Search .......... 422/22; 204/548, 608, 572, 571, 450; 604/6.04; 209/127.1, 209/128, 212, 213; 435/372; 210/645, 748, 210/646, 905
See application file for complete search history.

(56) References Cited

U.S. PATENT DOCUMENTS

| 3,630,882 | A | * | 12/1971 | Dilworth, III ............... 204/608 |
| 3,705,100 | A | * | 12/1972 | Blatt et al. ................. 604/6.04 |
| 3,850,369 | A |   | 11/1974 | Bull et al. |
| 3,897,343 | A |   | 7/1975  | Ayres |
| 3,909,419 | A |   | 9/1975  | Ayres |
| 3,931,018 | A |   | 1/1976  | North, Jr. |
| 3,982,691 | A |   | 9/1976  | Schlutz |
| 4,187,979 | A |   | 2/1980  | Cullis et al. |
| 4,322,298 | A |   | 3/1982  | Persidsky |
| 4,464,167 | A |   | 8/1984  | Schoendorfer et al. |
| 4,533,447 | A | * | 8/1985  | Meldon ....................... 204/548 |
| 4,675,117 | A |   | 6/1987  | Neumann et al. |
| 4,776,964 | A |   | 10/1988 | Schoendorfer et al. |
| 5,141,645 | A |   | 8/1992  | Shiraki et al. |
| 5,147,290 | A |   | 9/1992  | Jonsson |
| 5,370,802 | A |   | 12/1994 | Brown |
| 5,403,272 | A |   | 4/1995  | Deniega et al. |
| 5,454,472 | A | * | 10/1995 | Benecke et al. .......... 209/127.1 |
| 5,494,578 | A |   | 2/1996  | Brown et al. |
| 5,494,592 | A |   | 2/1996  | Latham, Jr. et al. |
| 5,601,727 | A |   | 2/1997  | Bormann et al. |
| 6,051,146 | A |   | 4/2000  | Green et al. |
| 6,537,433 | B1| * | 3/2003  | Bryning et al. ............. 204/450 |
| 7,011,790 | B2| * | 3/2006  | Ruan et al. ................. 422/22 |
| 7,115,205 | B2|   | 10/2006 | Robinson et al. |
| 7,211,037 | B2|   | 5/2007  | Briggs et al. |
| 2003/0134416 | A1 | * | 7/2003 | Yamanishi et al. ......... 435/372 |

* cited by examiner

*Primary Examiner*—Krishnan S Menon
*Assistant Examiner*—Marjorie Christian

(57) ABSTRACT

The separation of platelets from whole blood or any of its components Through electricity-based and/or mixed-phase effects.

1 Claim, 6 Drawing Sheets

Figure 6
Figure 6A
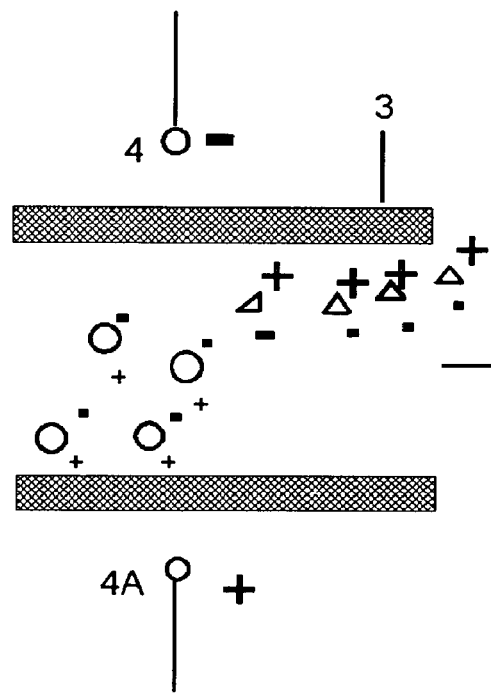
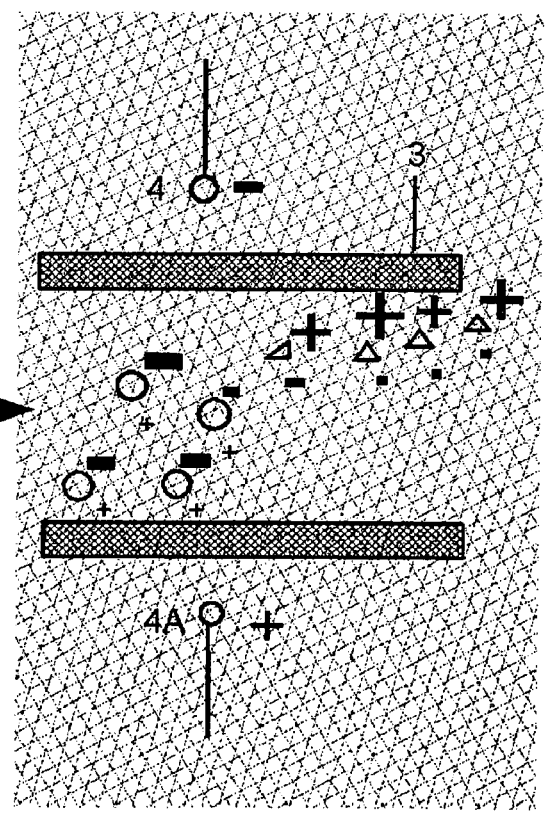

APPARATUS TO ASSIST PLATELET MANIPULATION TO PREVENT AND TREAT ENDOVASCULAR DISEASE AND ITS SEQUELAE

RELATED APPLICATIONS

Not applicable (no provisional or otherwise related applications)

STATEMENT REGARDING FEDERALLY SPONSORED RESEARCH OR DEVELOPMENT

Not Applicable (No federal Government Sponsorship or Involvement)

Names of Parties to a Joint Research Agreement

Not Applicable (No Joint Research Agreement in Effect)

Incorporation By Reference Of Material Submitted On A Compact Disk

Not Applicable (No Ancillary Electronic Data Appended)

TECHNICAL FIELD

Blood components processor, mixed phase electrophoresis.

BACKGROUND OF THE INVENTION

Cardiac and vascular disease (and, specifically, atherosclerosis) have emerged as the number one killer of modern man. It is a disease of multiple risk factors, but without a proven etiology.

Regarding the currently prevailing theory of cholesterol metabolism Disarray as the most important causative factor in the genesis of cardiac and vascular disease, it is remarkable that no one has ever proposed a logical justification for the existence of increased cardiovascular risk linked to the presence of increased cholesterol. The presence of such an ontological explanation would serve to bolster the selection of cholesterol as a causative factor, rather than merely as a factor associated with increased risk of vascular disease.

It is obvious, on the other hand, why animals of many species should have inordinately high platelet counts, in excess of what might be physiologic for long mammalian lives. Even while human beings had developed the genetic capacity for long lives in prehistoric times, trauma and infection were by far the most important mechanisms of demise. Life expectancies did not pass the three decade mark in many societies until the mid 19th century and continue to remain around this figure in several undeveloped nations today. Given these factors, it is obvious that the ability to achieve rapid and effective hemostasis would far outweigh the need for reduced intravascular events in nature. It is thus logical to assume that if the coagulation cascade can be demonstrated to be a participant in the development of vascular disease—which it is known to be—then it is likely that the survival traits of rapid hemostasis have long been in conflict with the requirements of long term patency. In other words, the "coagulation thermostat" has been selected for maximum rapidity and efficacy and this is in direct conflict with what is required for optimal blood vessel patency.

It is recognized from the experience of the primary applicant of this patent, as well as multiple other cardiovascular physicians that no patient with normally functioning platelets and chronic counts significantly below normal has ever presented with cardiovascular disease, acute or chronic. In addition, it is known that patients with Glanzmann's thrombasthenia, a genetic abnormality preventing platelet activation, are also immune to this disease. It is further known that patients undergoing cardiovascular by pass ("perfusion") and extra-corporeal membrane oxygenation for the purpose of cardiothoracic surgery experience a phenomenon known as "pump head", heretofore of unknown etiology, but logically due to activated and microaggregated platelet clusters. Finally, it is fact that the process of hemodialysis activates platelets in a manner similar to the cardiovascular by pass machines—to the extent that most patients need to be heparinized—and that patients on hemodialysis have tremendously accelerated progression of atherosclerosis.

As is outlined above, clinical observations, as well as basic research, confirm that platelets have the ability to initiate inflammation and/or induce vascular damage. Activated platelets are not only more likely to do this, but they also release neurohumors that linger and alter the function of blood. It is further known that platelets are the most unstable of all cells in the body (Ref. 1, 2). Even machines designed for the expressed purpose of platelet separation also cause significant degrees of platelet activation (at least 13% during the full separation by one account—Reference 3). This is because platelets are sticky, fragile and have multiple modes of activation. It is also due to the fact that prior art refers only to various centrifuge-based separation of platelets. Differential current and/or mixed phase processes are much more likely to effect rapid separation without current levels of platelet activation.

Substances released by activated platelets and retained in blood products also contribute to transfusion reactions, the onset or exacerbation of congestive heart failure, pneumonitis, pneumonia or other respiratory distress, as well as worsening of Systemic Inflammatory Response (SIRS) and frank sepsis.

Further, there is evidence that the initial establishment of tumors is not possible without angiogenesis. In addition, there is evidence that thrombin receptors have a role in this initial angiogenesis. Platelets have a role in modulation of thrombin receptors. Reduction of platelets to safe levels would affect thrombin receptor levels.

Finally, for anyone in doubt of the veracity of the potency of platelet effect on fibroblast growth and selected cellular activity, refer to U.S. Pat. No. 5,165,938. Platelet extracts cause visible increase in fibroblast activity that can be demonstrated through gross cell culture assays. Platelets (and compounds released by platelets) have a similar inflammatory effect on white cells and multiple other blood and vascular components.

Lexicon

DEFINITIONS

Platelets are the smallest components of whole blood and have a role in the initiation of coagulation, as well as the formation of clots.

Red blood cells are larger, enucleated, hemoglobin-bearing cells with the primary function of carrying oxygen and carbon dioxide.

White cells are those particulate components of blood that are neither platelets, nor red blood cells.

Inert or neutral material is to be understood to include any substance that would result in minimal (less than 1%) unprovoked platelet activation during the entire time of transit through the separation apparatus.

Where unprovoked platelet activation, in contrast to provoked platelet activation, would consist of the activation of a significant proportion (>0.5%) of platelets in the absence of a mechanical or chemical stimuli known to reproducibly cause platelet activation.

Chemical and mechanical stimuli known to reproducibly cause platelet activation to include any and all components of the coagulation cascade, uncoated glass and plastic surfaces, pharmacologic substances resulting in platelet aggregation and/or degranulation, any fine particulates or large molecular weight molecules capable of forming a nidus for platelet aggregation, as well as any mechanical factors such as turbulence known to result in platelet activation and/or degranulation.

Anti-activation compounds to include all solvents and pharmaceuticals known to inhibit the degranulation and activation of platelets.

Mixed phase reactions are the combination of non-miscible or partially miscible compounds, some in different states of matter such as gas versus liquids, preserving through their separation distinct transition interfaces.

"Vascular disease and its sequelae" includes atherosclerosis of all types and etiologies, intimal injury of any nature and etiology, other vessel wall injury, whether acute or chronic or whether involving large areas or microscopic segments and of any etiology. Vascular disease for the purposes of this patent may exclude acute vasoocclusive conditions and concentric intimal hyperplasia with luminal narrowing, as specified by U.S. Pat. Nos. 6,376,242, 6,585,995 & 7,022,521, but only for the specific matrix of interventions as specified in those two patents. Specifically, exchange transfusion or extracorporeal platelet manipulation in this setting shall be included in the definition, since only pharmacologic platelet reduction is included in the claims of this prior art.

"Vascular disease and its sequelae" also includes thrombotic, embolic or other particulate based conditions. Specifically, vascular disease shall also be deemed to include the specific cardiac diagnoses of Atrial Fibrillation and any other cardiac conditions leading to arrhythmias (such as cardiac non-compaction and ARVD—Arrhythmogenic Right Ventricular Dysplasia—to name a few).

"Vascular disease and its sequelae" is to include adult, foetal and congenital conditions.

"Vascular disease and its sequelae" is applicable to all species.

"Vascular disease and its sequelae" shall comprise all conditions that affect the function of all components of blood and lymphatic vessels and that result in or contribute to any harmful consequences to the organism, whether such a linkage may be presently recognized or not. One particular for instance would be Alzheimer's disease, which is probably caused by microvascular emboli and thrombosis and would thus fall in the category of "sequelae".

Vascular disease and its sequelae" also includes all pathologic states to which such disease might contribute, whether such linkage may currently be recognized or not. While understood that this list is not comprehensive, such sequelae would include obstruction, embolization, thrombosis, reduced blood flow, inflammatory states, chronic pain and reduced function to any body organs. Sequelae of vascular disease shall further include plaque and neurofibrillary deposits on macroscopic or microscopic scale, microvascular states, potentiation of metabolic disorders, tissue acidosis, as well as general ill-described malaise and failure to recover appropriately after stress conditions. Sequelae of vascular disease shall include a (past, present or future) history of cerebrovascular accidents, macrovascular or microvascular CNS disease, whether it be hypertensive, diabetic, or at present unknown etiology. Potential sequelae of vascular disease are to specifically include all malignancy states, whether overtly perfusion dependent or not. Sequelae of vascular disease are also to be assumed to include microvascular cardiac and peripheral disease ("Syndrome X") and Burger's disease (endarteritis obliterans), as well as Alzheimer's and other microvascular CNS pathology. Additionally, sequelae of vascular disease for the purpose of this patent is include diseases such as ITP and HUS/TTP and their heretofore unrecognized analogues. Finally, sequelae of vascular disease will also include SIRS (systemic inflammatory response syndrome), as well as frank sepsis.

BACKGROUND ART

There are no prior or proposed devices to separate isolate platelets from blood or its components through the use of electricity or mixed phase reactions.

BRIEF SUMMARY OF THE INVENTION

The separation of platelets from whole blood or any of its components through electricity-based and/or mixed-phase effects is proposed.

Anticoagulated and/or diluted blood is introduced into the acceptance chamber, from where it transits into the separation chamber. A voltage is applied to this chamber in a direction transverse to the flow of blood. Platelets and plasma are forced through the semi-permeable membrane into that portion of the chamber not accessible to larger blood components and clumped platelet aggregates.

DESCRIPTION OF THE DRAWINGS

FIGS. 6 and 6A (side cross view) illustrates the principle of differential charge accumulation in an electromagnetic field. Legend is as in prior figures. Item 12 represents the application of an electromagnetic field. The crosshatching in FIG. 6A represents the electromagnetic field present within the apparatus.

DETAILED DESCRIPTION OF THE INVENTION

Figure 1:
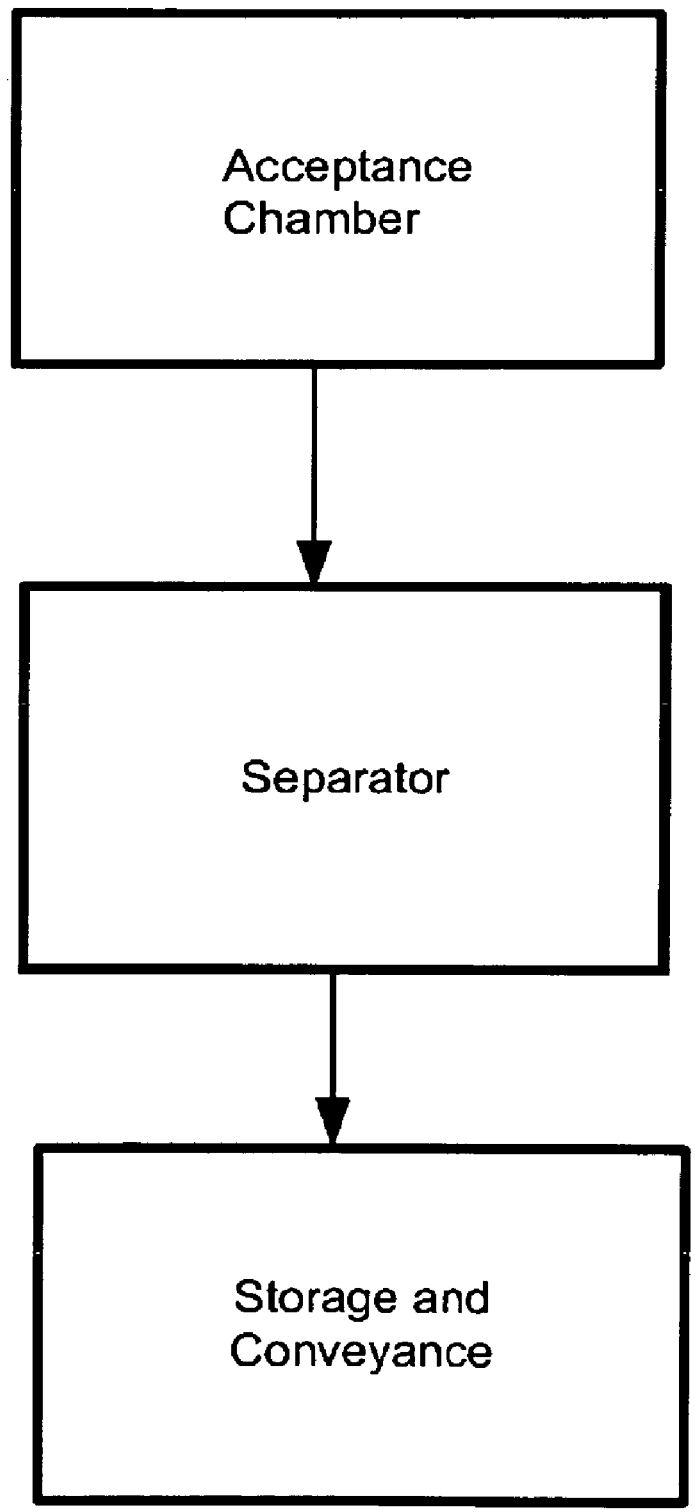
FIG. 1 is a schematic flow chart of the sequence of separation steps. The presentation is in text-box format and no separate labels are provided.
Figure 2:
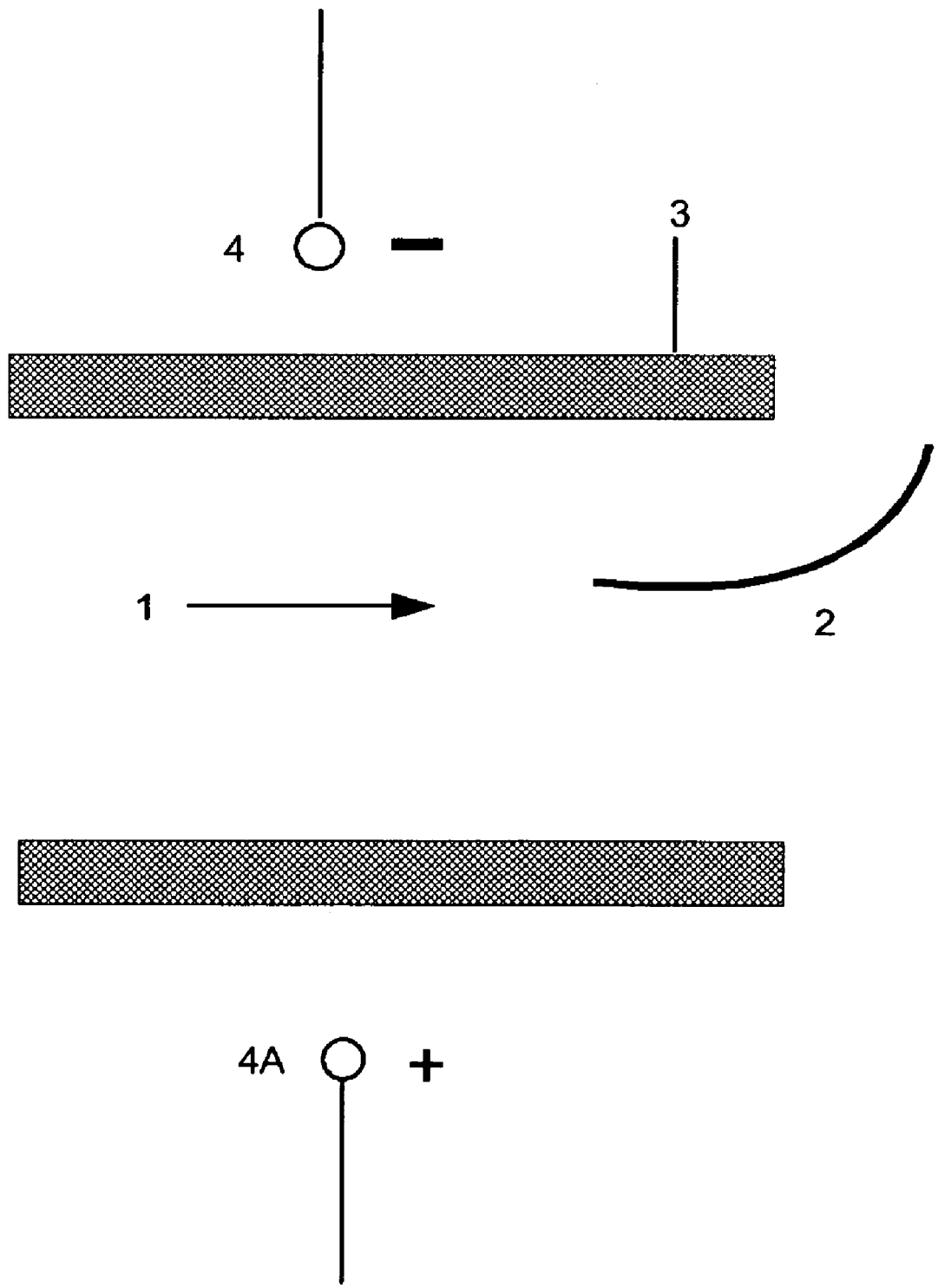
FIG. 2 illustrates a cross section of the platelet separator in side view. Item 1 is the direction of blood flow, Item 2 (optional) is a baffle separator utilized in continuous process production, Item 3 is one of the chamber walls, Item 4 and 4a are the negative and positive electrodes, respectively. Please Note: the separator baffle is used primarily for continuous process separation; chambers are physically divided for batch processes, separated by selectively permeable membranes.
Figure 3:
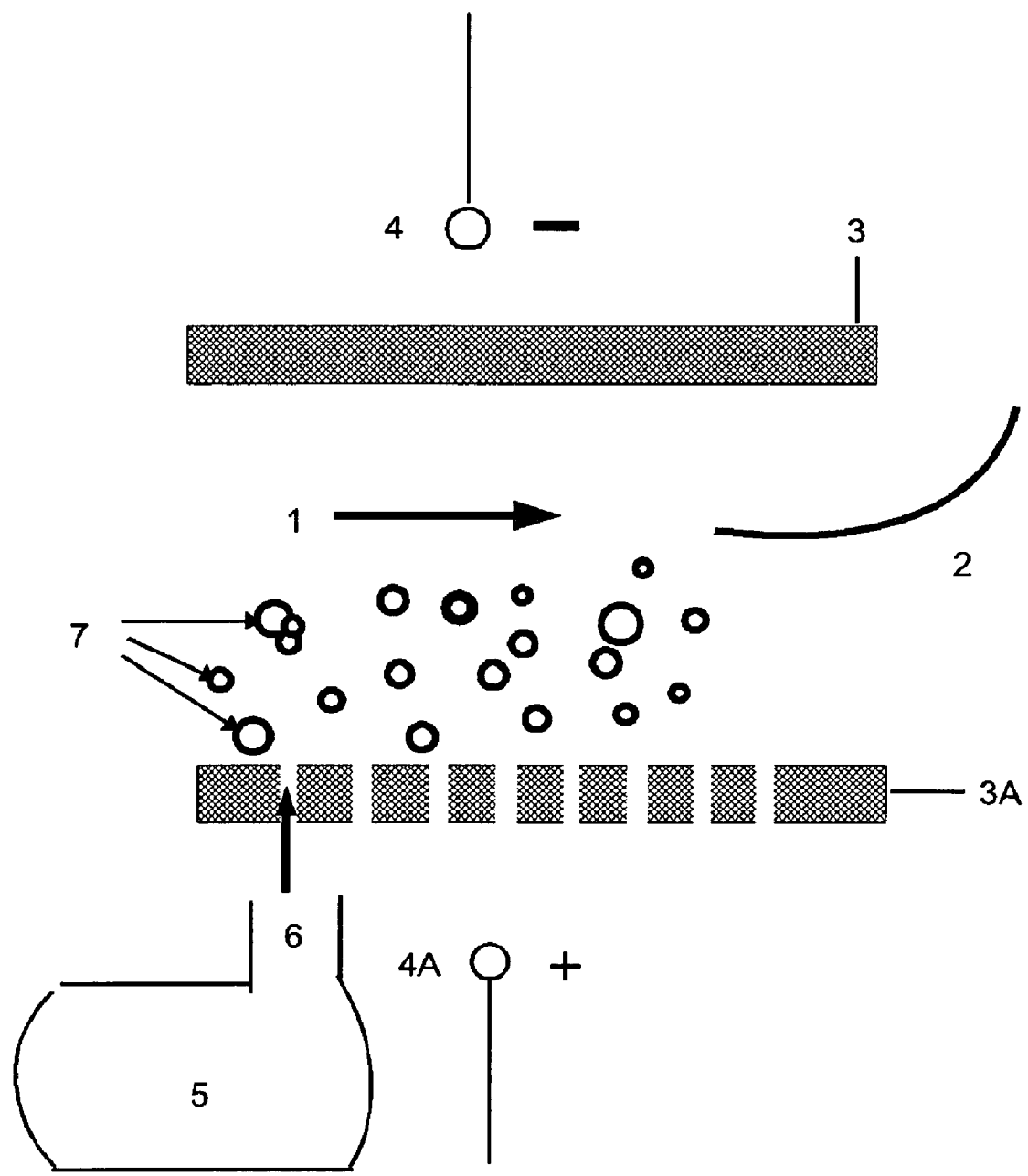
FIG. 3 illustrates a cross section of the same platelet separator as FIG. 2, but now enhanced with additional mixed phase separation, in side view. Same legend as in FIG. 2. Additional Item 3A is a bubble plate (or other type of selectively permeable plate permitting the transmission of the secondary separating phase), Item 5 is a reservoir for Nitrogen Gas (or another gas or another working fluid utilized as a secondary separator), Item 6 is the path of the secondary separation gas/liquid to the bubble plate and Item 7 is bubble (or other mixed phase micelles). Please Note: the presence of a separator plate implies a continuous separation process.
Figure 4:
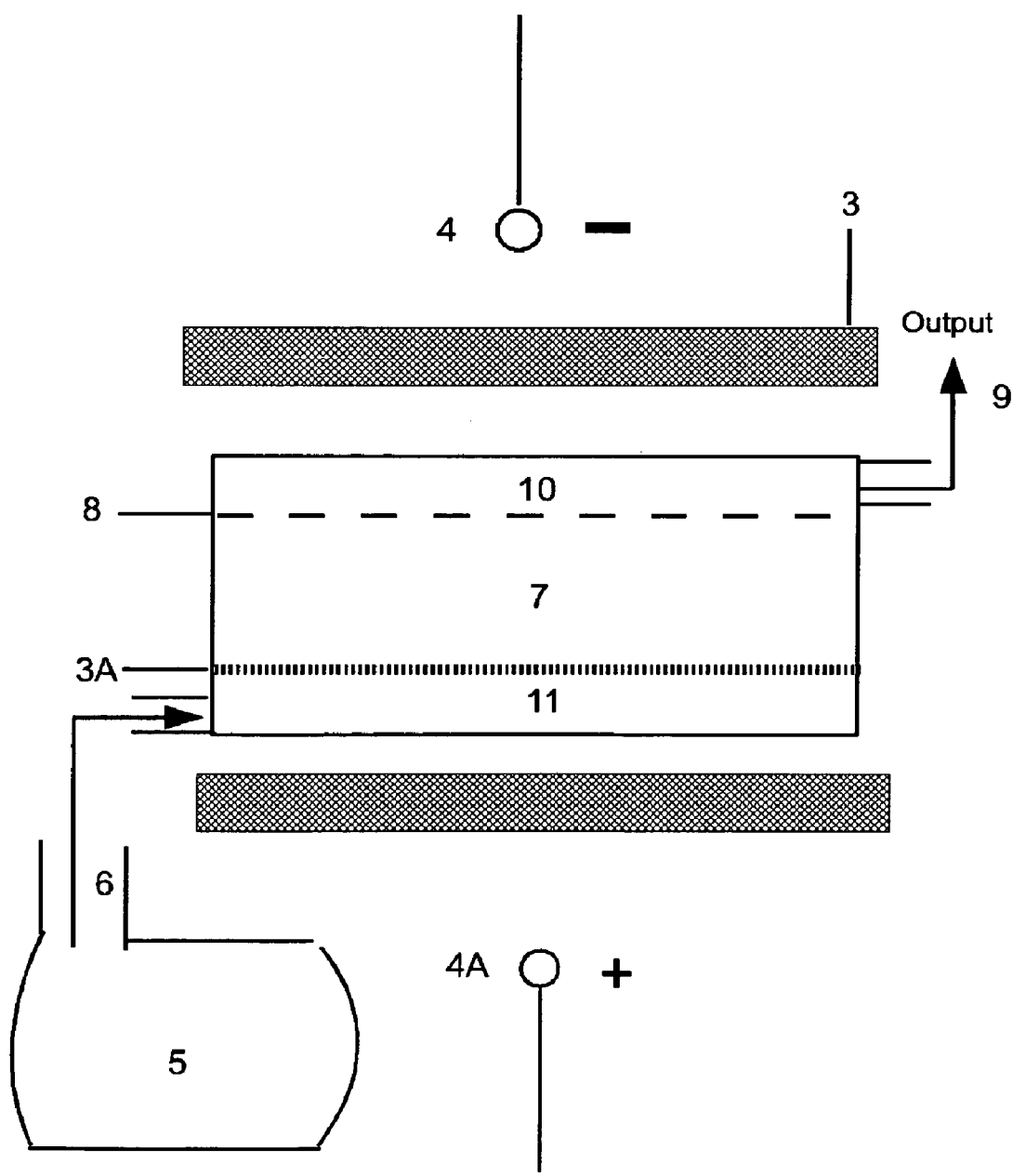
FIG. 4 (side cross section) demonstrates an embodiment comprising a 3 chamber separation bag for a batch separation process. Same legend as in FIGS. 2 and 3, with additional Item 8 is a selectively permeable membrane that permits transit of platelets and gas, Item 9 is the output stream, Item 10 is the platelet rich separated layer and Item 11 is the potential space created by the selectively permeable membrane that conducts the secondary separating fluid into the main body of the chamber. Please note that Item 5 in this case is somewhat different from the prior illustrations in that it is not integrated into the wall of the separation chamber, but rather into the separate bag utilized for the batch separation process.
Figure 5:
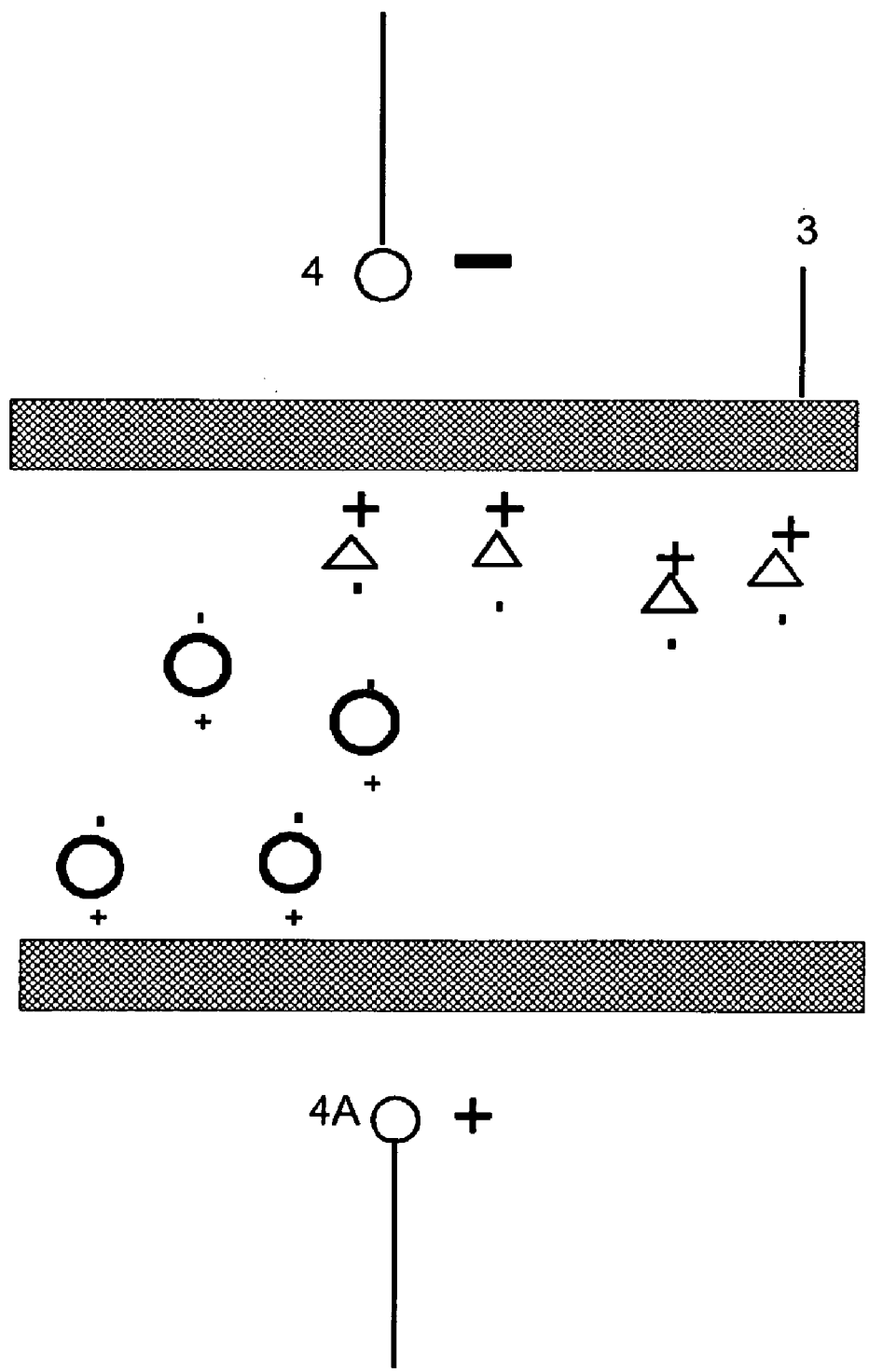
FIG. 5 (side cross view) demonstrates the operating principle of the apparatus. Legend is as in prior Figures. Additionally, the circles represent larger blood cells (primary red cells, but also white cells), whereas the triangles represent platelets. Since platelets and red cells have different affinities for changes (and different CAPACITANCE), the charges accumulated in an electric field will differ (Electromagnetic radiation enhances this charge differential). Additionally, platelets are also much smaller, so they move more readily (i.e.: they accelerate more easily) and with a higher maximum velocity in an electric field.

Anticoagulated and/or diluted blood is introduced into the acceptance chamber, from where it transits into the separation chamber. A voltage is applied to this chamber in a direction transverse to the flow of blood. Platelets and plasma are forced through the semi-permeable membrane into that portion of the chamber not accessible to larger blood components and clumped platelet aggregates.

Appropriate pore size membranes are readily available at present and shall not be dwelled upon in detail. Further discussion shall focus on adjunct methods of increasing throughput and efficiency.

Proper buffering and anticoagulation of blood with agents such as heparin and EDTA may be necessary. The dilution of plasma with large amounts of saline is advisable. This plasma can later be reclaimed through ultrafiltration or other reclamation methods.

The transition of non-miscible liquids of very small droplet sizes through the chamber may be useful to perform an initial separation and to thus accelerate the yield of the process. These droplets can then be re-separated either through a passive process (such as settling) or an active one (such as centrifugation) (of note, this centrifugation would be only for the purpose of separating the mixed phase and would thus be much gentler than the centrifugation required to separate individual blood components).

The injection of carbonic acid or other liquid that would result in gas release, or the transition of gas bubbles of extremely small particle size (such as produced through the use of ultrasound), would result in a similar phenomenon. Platelets are likely to settle on the mixed-phase interface at a much higher rate than the much larger PRBC's, particularly if a charge is deposited on their surface.

Contrary to what might be initially guessed, though platelets are much smaller than PRBCs, they are unlikely to move at a sufficiently different rate in a liquid then PRBC's under the influence of a simple electrical field. This is because there is a very large amount of fluid drag to hinder the movement of such tiny particles. For this reason, there must be the initial application of an electromagnetic field of suitable frequency to the separation chamber. Such fields result in the entrapment of various partial charges on the individual surfaces contained within the flux and would enhance any base difference in platelet versus PRBC base charge. Combined with the difference in the mobility of platelets, this will result in sufficient separation to be of clinical use.

A further improvement of the art might be the addition of an orthogonal magnetic field to steer red cells, which are paramagnetic due to their hemoglobin content. This would result in the movement of cells along an axis coincident with the exit route of red blood cells, passively sweeping along white cells.

Pre-dilution or intra-separation dilution of blood during centrifugation has been described. This may also be of utility in the currently proposed technology. Multiple stages are likely to increase both the efficacy (i.e.: maximum extracted yield), as well as efficiency (i.e.: velocity of extraction and required volumetric capacity of the separation apparatus).

An electronic piece of equipment is likely to be both more compact and easier to operate than the standard available centrifugation apparatus. For this reason it's likely more adaptable to current and future procedures, such as surgeries. It is also envisioned to be of great utility in plasma exchange and plateletpheresis for the purpose of conditions such as TTP (thrombotic thrombocytopenic purpura).

The invention claimed is:

1. An apparatus for the separation of platelets from blood comprising:
   a chamber through which blood can flow;
   parallel electrodes on the top and bottom of the chamber and spaced apart across blood flow path, the parallel electrodes capable of producing a radio frequency modulated electrostatic field perpendicular to the blood flow direction;
   the bottom electrode comprising a plurality of holes for admitting bubbles of an inert gas into the blood stream; and
   a source of inert gas coupled to the bottom electrodes.

* * * * *